(12) United States Patent
Mentak

(10) Patent No.: US 7,857,848 B2
(45) Date of Patent: Dec. 28, 2010

(54) INFINITE REFRACTIVE INDEX GRADIENT (IRIG) POLYMERS FOR OCULAR IMPLANT AND CONTACT LENS APPLICATIONS

(75) Inventor: Khalid Mentak, San Ramon, CA (US)

(73) Assignee: Key Medical Technologies, Inc., San Ramon, CA (US)

( * ) Notice: Subject to any disclaimer, the term of this patent is extended or adjusted under 35 U.S.C. 154(b) by 1013 days.

(21) Appl. No.: 11/388,212

(22) Filed: Mar. 23, 2006

(65) Prior Publication Data

US 2007/0004863 A1    Jan. 4, 2007

Related U.S. Application Data

(60) Provisional application No. 60/677,917, filed on May 5, 2005.

(51) Int. Cl.
  *A61F 2/14*  (2006.01)
  *A61F 2/16*  (2006.01)
  *G02C 7/10*  (2006.01)
  *G02C 7/06*  (2006.01)
  *G02B 1/04*  (2006.01)
  *C08F 2/00*  (2006.01)

(52) U.S. Cl. ............... 623/4.1; 623/6.11; 351/159; 351/166; 523/106; 526/72

(58) Field of Classification Search ........... 428/447; 528/43; 427/2.24; 623/6, 11.6, 13; 351/159, 351/171, 166; 523/106; 526/72
See application file for complete search history.

(56) References Cited

U.S. PATENT DOCUMENTS

| | | | |
|---|---|---|---|
| 4,304,895 A | | 12/1981 | Loshaek |
| 4,528,311 A | | 7/1985 | Beard et al. |
| 4,856,889 A | | 8/1989 | Guilino et al. |
| 5,374,663 A | | 12/1994 | Daicho et al. |
| 5,470,932 A | | 11/1995 | Jinkerson |
| 5,528,322 A | | 6/1996 | Jinkerson |
| 5,543,504 A | | 8/1996 | Jinkerson |
| 5,662,707 A | | 9/1997 | Jinkerson |
| 5,861,934 A | | 1/1999 | Blum et al. |
| 6,089,711 A | | 7/2000 | Blankenbecler et al. |
| 6,138,479 A | | 10/2000 | Gille et al. |
| 6,353,069 B1 * | | 3/2002 | Freeman et al. ............ 526/319 |
| 6,695,880 B1 | | 2/2004 | Roffman et al. |
| 6,815,074 B2 * | | 11/2004 | Aguado et al. ............ 428/447 |

OTHER PUBLICATIONS

Acrysof® Natural single piece IOL, Product Monograph © 2004 by Alcon Laboratories, Inc.

* cited by examiner

*Primary Examiner*—Ling-Siu Choi
*Assistant Examiner*—Monique Peets
(74) *Attorney, Agent, or Firm*—Whyte Hirschboeck Dudek S.C.; Grady J. Frenchick

(57) ABSTRACT

Infinite gradient refractive index ophthalmic devices and methods of making same. The method involves diffusing a monomer which polymerizes to a lower or higher corresponding opposite refractive index polymer into a lower or higher index polymer structure and polymerizing same to create the gradient structure. The resulting polymeric structure is used to manufacture ophthalmic devices, e.g., intraocular lenses.

3 Claims, 3 Drawing Sheets

_US 7,857,848 B2_

INFINITE REFRACTIVE INDEX GRADIENT (IRIG) POLYMERS FOR OCULAR IMPLANT AND CONTACT LENS APPLICATIONS

FIELD OF THE INVENTION

The present invention relates to ophthalmic lenses in general and intraocular lenses (IOLs) in particular and to a method for making and using the same. More particularly, the present invention relates to mutlifocal IOLs with a certain level of accommodation designed for refractive correction in aphakic eyes where a diseased natural lens is surgically removed, such as in the case of cataracts.

BACKGROUND OF THE INVENTION

IOL implants have been used for many years in aphakic (i.e. absent lens) eyes as replacements for diseased natural crystalline lenses that have been surgically removed from the eyes. Many different IOL designs have been developed over past years and proven successful for use in aphakic eyes. Successful IOL designs to date primarily include an optic portion with supports therefore, called haptics, connected to and surrounding at least part of the optic portion. The haptic portions of an IOL are designed to support the optic portion of the IOL in the lens capsule, anterior chamber or posterior chamber of an eye.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs are subject to compressive forces exerted on the outer edges thereof from natural brain-induced contraction and relaxation of the ciliary muscle and increases and decreases in vitreous pressure. Compressive forces of this kind are useful in a phakic eye for focusing the eye at various distances. Most commercially successful IOL designs for use in aphakic eyes have single focus optic portions that are fixed and focus the eye at only a certain fixed distance. Such single focus IOLs require the wearing of glasses to change the focus of the eye few bifocal IOLs have been introduced to the commercial market but suffer from the disadvantage that each bifocal image represents only about forty percent of the available light and the remaining twenty percent of the light is lost to scatter, which provides lessened visual acuity.

Because of the noted shortcomings of current IOL designs, there is a need for IOLs designed to provide multifocal visual imaging in aphakic eyes without the aid of eyeglasses.

Current multifocal IOLs are based on integrating a few optical zones within the IOL surface to create a limited number of focal points on the cornea, e.g. U.S. Pat. Nos. 6,695,880 and 6,089,711. Each focal point or zone offers corrected vision at a specific distance (near, intermediate, and far). Accommodating IOLs are designed to simulate the performance of the healthy natural lens when the focus shifts from far to near or vice versa by allowing the IOL to move within the eye. Neither type of lenses performs satisfactorily.

The present invention is based on the novel concept that making an IOL with a true infinite refractive index gradient (IRIG) would provide patients with improved near, far and intermediate vision. In fact, the human natural lens has a true IRIG that is responsible for accommodation, depth of field perception and contrast sensitivity. More importantly, the contribution of IRIG to the lens power of the natural lens decreases significantly with age at a rate of $0.286 \pm 0.067$ diopter per year (ref). This change accounts almost entirely for the estimated overall loss of accommodation responsible for presbyopia and loss of contrast sensitivity. An IOL similar in IRIG to a healthy human natural lens would restore accommodation and adequate vision to cataract patients.

SUMMARY OF THE INVENTION

An ophthalmic device, e.g. a multifocal intraocular lens (IOL), made in accordance with the present invention is made from a polymeric material having a true IRIG. A true refractive index (RI) gradient is described as an RI, which decreases infinitesimally in one preferred direction (or increases infinitesimally), forming a continuum or gradient of infinite values from ophthalmic device edge to center (or center to edge). This embodiment of the invention mimics a healthy human natural lens, which provides normal accommodation for far, intermediate, and near vision with no distortion, loss of depth of field, or unwanted images such halos, bright spots or light scattering produced by discrete RI interfaces or changes between optical zones with a single RI.

In a further aspect, the present invention is a method for making IRIG ophthalmic devices.

In yet a further aspect, the present invention is IRIG intraocular lenses (IOLs) and methods for making same.

In yet another aspect, the present invention is a multifocal ophthalmic lens;

Accordingly, it is an object of the present invention to provide a multifocal intraocular lens with accommodation capabilities for use in aphakic eyes.

Another object of the present invention is to provide multifocal intraocular lenses for use in aphakic eyes, which minimize optical distortions, halos, and loss of depth of field.

Another object of the present invention is to provide multifocal intraocular lenses for use in aphakic eyes, which minimize existing optical aberrations.

Still another object of the present invention is to provide accommodating intraocular lenses capable of improving contrast sensitivity.

The method used to produce the lens of the present invention is as follows:

1. The first step involves producing the core material at the center of the IOL, which contains a higher RI copolymer. A rod measuring approximately 6 inches in length and 6 mm in diameter is produced by polymerizing a base polymer or base material having a RI between 1.30 and 1.7. The polymer rod is removed from the mold without allowing the polymerization to proceed to completion.

2. The second step involves placing the rod produced in step 1 in a center of a cylindrical mold measuring, for example, 6 inches (15.24 mm) in length and 10 mm in diameter. A solution of a lower refractive index monomer is allowed to diffuse or permeate into the base polymer to create a gradient RI and then polymerized around the 6 mm rod to create a monolithic polymer rod measuring 6 inches (15.24 mm) in length and about 10 mm in diameter and having a IRIG created by the fickian nature of the diffusion of the lower RI monomer into the higher RI polymer rod.

The polymer rod is machined into 17 mm×2 mm disks and IOLs were cut from the samples. This method creates IOLs with an IRIG suitable for multifocal accommodating lenses. It will be appreciated by one skilled in this art that the lens or optic part of many other types of ophthalmic devices could be prepared using the above-disclosed and below-illustrated process. All such devices are within the scope of the present invention.

BRIEF DESCRIPTION OF THE DRAWINGS

The invention will now be described with reference to the attached drawings in which like features are indicated by like numerals.

DETAILED DESCRIPTION OF THE INVENTION

Base Materials

Figure 1:
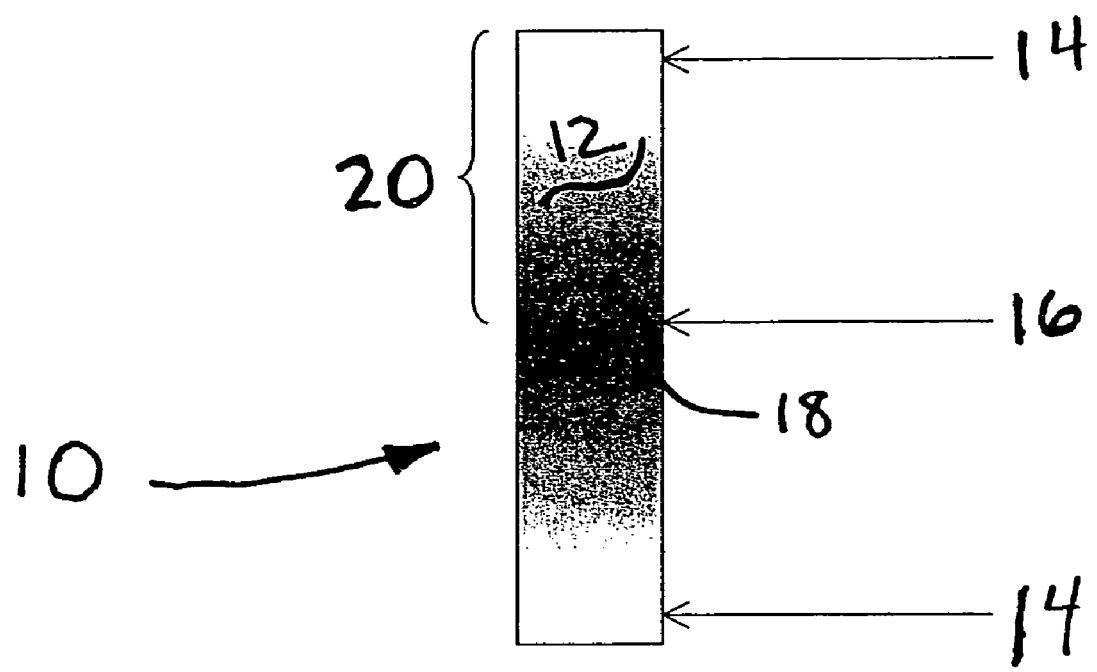
FIG. 1 is a schematic cross-sectional representation of a button, lens, ophthalmic device employing an IRIG polymer and illustrating the infinite gradient refractive index.

Suitable lens-forming monomers for use in the present invention include carbazole and/or naphthyl moiety, carbazole, naphthalene, or a naphthyl group such as vinyl carbazole, vinyl naphthalene, lauryl methacrylate, stearyl methacrylate, methyl methacrylate, 2-hydroxyethyl acrylate, 2-hydroxyethyl methacrylate, 3-hydroxypropyl acrylate, 3-hydroxypropyl methacrylate, n-vinyl pyrolidone, styrene, eugenol (4-hydroxyvinylbenzene), .alpha.-methylstyrene. In addition, for high-refractive index foldable lens applications, suitable monomers include, but are not limited to: 2-ethylphenoxy methacrylate, 2-ethylphenoxy acrylate, 2-ethylthiophenyl methacrylate, 2-ethylthiophenylacrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates. N-vinyl pyrolidone, styrene, eugenol and .alpha.-methyl styrene may also be suitable for high-refractive index foldable lens applications.

A preferred lens-forming monomer mixture is the mixture of vinyl carbazole, lauryl methacrylate, and hydroxyethyl acrylate.

The copolymerizable cross-linking agent used in the lens-materials of this invention may be any terminally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is ethylene glycol dimethacrylate.

Suitable crosslinkers also include polymeric crosslinkers, such as, polyethylene glycol 1000 diacrylate, polyethylene glycol 1000 dimethacrylate, polyethylene glycol 600 dimethacrylate, polybutanediol 2000 dimethacrylate, polypropylene glycol 1000 diacrylate, polypropylene glycol 1000 dimethacrylate, polytetramethylene glycol 2000 dimethacrylate, and polytetramethylene glycol 2000 diacrylate.

An ultra-violet absorbing material can also be included in the polymeric lenses of this invention in order that the lenses may have an ultraviolet absorbance approximately equivalent to that of the natural lens of the eye. The ultraviolet absorbing material can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include vinyl anthracene, substituted benzophenones, such as 2-hydroxybenzophenone, and 2-(2-hydroxyphenyl)benzotriazoles. It is preferred to use an ultraviolet absorbing compound which is copolymerizable with the monomers and is thereby covalently bound to the polymer matrix. In this way possible leaching of the ultraviolet absorbing compound out of the lens and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5' methyl phenyl)benzotriazole and vinyl anthracene.

Ultraviolet and/or blue light absorbing chromophores may be added to the base polymer. Such chromophores can be any compound which absorbs violet/blue light, i.e., light having a wavelength between about 380 nm and 570 nm. Yellow and orange dyes, polymerizeable yellow and orange dyes, chromene, and any combination thereof. The preferred BLCB is a combination of vinyl anthracene and disperse orange 3 methacrylamide.

Lower RI Monomer

Monomers useful for this invention are those capable of forming a homopolymer with a glass transition temperature (Tg) equal or lower than 25° to allow for the production of a foldable lens. The primary requirement for selection of a lower RI monomer is that the RI of the corresponding homopolymer should be less than that of the base polymer and, of course, be capable of coupling to the base polymer, e.g., co-polymerizing therewith, to produce a material that does not elute of otherwise emit monomer or polymer constituents. Monomers useful for this invention include acrylate and methacrylate derivatives including:

| Polymer | Refractive Index |
|---|---|
| Poly(pentadecafluorooctyl acrylate) | 1.3390 |
| Poly(tetrafluoro-3-(heptafluoropropoxy)propyl acrylate) | 1.3460 |
| Poly(tetrafluoro-3-(pentafluoroethoxy)propyl acrylate) | 1.3480 |
| Poly(undecafluorohexyl acrylate) | 1.3560 |
| Poly(nonafluoropentyl acrylate) | 1.3600 |
| Poly(tetrafluoro-3-(trifluoromethoxy)propyl acrylate) | 1.3600 |
| Poly(pentafluorovinyl propionate) | 1.3640 |
| Poly(heptafluorobutyl acrylate) | 1.3670 |
| Poly(trifluorovinyl acetate) | 1.3750 |
| Poly(octafluoropentyl acrylate) | 1.3800 |
| Poly(pentafluoropropyl acrylate) | 1.3850 |
| Poly(2-heptafluorobutoxy)ethyl acrylate) | 1.3900 |
| Poly(chlorotrifluoroethylene) | 1.3900 |
| Poly(2,2,3,4,4-hexafluorobutyl acrylate) | 1.3920 |
| Poly(trifluoroethyl acrylate) | 1.4070 |
| Poly(2-(1,1,2,2-tetrafluoroethoxy)ethyl acrylate) | 1.4120 |
| Poly(trifluoroisopropyl methacrylate) | 1.4177 |
| Poly(2,2,2-trifluoro-1-methylethyl methacrylate) | 1.4185 |
| Poly(2-trifluoroethoxyethyl acrylate) | 1.4190 |
| Poly(trifluoroethyl methacrylate) | 1.4370 |
| Poly(methyl octadecyl siloxane) | 1.4430 |
| Poly(methyl hexyl siloxane) | 1.4430 |
| Poly(methyl octyl siloxane) | 1.4450 |
| Poly(isobutyl methacrylate) | 1.4470 |
| Poly(vinyl isobutyl ether) | 1.4507 |
| Poly(methyl hexadecyl siloxane) | 1.4510 |
| Poly(vinyl ethyl ether) | 1.4540 |
| Poly(methyl tetradecyl siloxane) | 1.4550 |
| Poly(vinyl n-butyl ether) | 1.4563 |
| Poly(3-hexoxypropylene oxide) | 1.4590 |
| Poly(ethylene glycol) | 1.4590 |
| Poly(vinyl n-pentyl ether) | 1.4590 |
| Poly(vinyl n-hexyl ether) | 1.4591 |
| Poly(4-fluoro-2-trifluoromethylstyrene) | 1.4600 |
| Poly(vinyl octyl ether) | 1.4613 |
| Poly(vinyl n-octyl acrylate) | 1.4613 |
| Poly(vinyl 2-ethylhexyl ether) | 1.4626 |
| Poly(vinyl n-decyl ether) | 1.4628 |
| Poly(2-methoxyethyl acrylate) | 1.4630 |
| Poly(acryloxypropyl methyl siloxane) | 1.4630 |
| Poly(4-methyl-1-pentene) | 1.4630 |
| Poly(3-methoxypropylene oxide) | 1.4630 |
| Poly(t-butyl methacrylate) | 1.4638 |
| Poly(vinyl n-dodecyl ether) | 1.4640 |
| Poly(3-ethoxypropyl acrylate) | 1.4650 |
| Poly(vinyl propionate) | 1.4664 |
| Poly(vinyl acetate) | 1.4665 |
| Poly(vinyl propionate) | 1.4665 |
| Poly(vinyl methyl ether) | 1.4670 |
| Poly(ethyl acrylate) | 1.4685 |
| Poly(vinyl methyl ether) | 1.4700 |
| Poly(3-methoxypropyl acrylate) | 1.4710 |
| Poly(1-octadecene) | 1.4710 |
| Poly(2-ethoxyethyl acrylate) | 1.4710 |
| Poly(isopropyl acrylate) | 1.4728 |
| Poly(1-decene) | 1.4730 |
| Poly(lauryl methacrylate) | 1.4740 |
| Poly(vinyl sec-butyl ether)(isotactic) | 1.4740 |
| Poly(n-butyl acrylate) | 1.4740 |
| Poly(dodecyl methacrylate) | 1.4740 |
| Poly(ethylene succinate) | 1.4744 |
| Poly(tetradecyl methacrylate) | 1.4746 |
| Poly(hexadecyl methacrylate) | 1.4750 |
| Poly(2-fluoroethyl methacrylate) | 1.4768 |
| Poly(octyl methyl silane) | 1.4780 |
| Poly(methyl acrylate) | 1.4793 |
| Poly(dicyanopropyl siloxane) | 1.4800 |
| Poly(sec-butyl methacrylate) | 1.4800 |
| Poly(dimethylsiloxane-co-alpha-methylstyrene) | 1.4800 |
| Poly(n-hexyl methacrylate) | 1.4813 |
| Poly(n-butyl methacrylate) | 1.4830 |
| Poly(ethylidene dimethacrylate) | 1.4831 |
| Poly(2-ethoxyethyl methacrylate) | 1.4833 |

-continued

| Polymer | Refractive Index |
|---|---|
| Poly(n-propyl methacrylate) | 1.4840 |
| Poly(ethyl methacrylate) | 1.4850 |
| Poly(vinyl butyral) | 1.4850 |
| Poly(3,3,5-trimethylcyclohexyl methacrylate) | 1.4850 |
| Poly(2-nitro-2-methylpropyl methacrylate) | 1.4868 |
| Poly(1,1-diethylpropyl methacrylate) | 1.4889 |
| Poly(triethylcarbinyl methacrylate) | 1.4889 |
| Poly(methyl methacrylate) | 1.4893 |
| Poly(mercaptopropyl methyl siloxane) | 1.4900 |
| Poly(ethyl glycolate methacrylate) | 1.4903 |
| Poly(3-methylcyclohexyl methacrylate) | 1.4947 |
| Poly(cyclohexyl alpha-ethoxyacrylate) | 1.4969 |
| Poly(4-methylcyclohexyl methacrylate) | 1.4975 |
| Poly(decamethylene glycol dimethacrylate) | 1.4990 |
| Poly(2-bromo-4-trifluoromethyl styrene) | 1.5000 |
| Poly(ethyl alpha-chloroacrylate) | 1.5020 |
| Poly(2-methylcyclohexyl methacrylate) | 1.5028 |
| Poly(bornyl methacrylate) | 1.5059 |
| Poly(ethylene glycol dimethacrylate) | 1.5063 |
| Poly(cyclohexyl methacrylate) | 1.5065 |
| Poly(cyclohexanediol-1,4-dimethacrylate) | 1.5067 |
| Poly(tetrahydrofurfuryl methacrylate) | 1.5096 |
| Poly(1-methylcyclohexyl methacrylate) | 1.5111 |
| Poly(2-hydroxyethyl methacrylate) | 1.5119 |
| Poly(1-butene)(isotactic) | 1.5125 |
| Poly(vinyl methacrylate) | 1.5129 |
| Poly(vinyl chloroacetate) | 1.5130 |
| Poly(N-butyl methacrylamide) | 1.5135 |
| Poly(2-chloroethyl methacrylate) | 1.5170 |
| Poly(methyl alpha-chloroacrylate) | 1.5170 |
| Poly(2-diethylaminoethyl methacrylate) | 1.5174 |
| Poly(2-chlorocyclohexyl methacrylate) | 1.5179 |
| Poly(allyl methacrylate) | 1.5196 |
| Poly(methacrylonitrile) | 1.5200 |
| Poly(N-2-methoxyethyl)methacrylamide | 1.5246 |
| Poly(2,3-dimethylbutadiene){methyl rubber} | 1.5250 |
| Poly(2-chloro-1-(chloromethyl)ethyl methacrylate) | 1.5270 |
| Poly(1,3-dichloropropyl methacrylate) | 1.5270 |
| Poly(acrylic acid) | 1.5270 |
| Poly(N-vinyl pyrrolidone) | 1.5300 |
| Poly(methyl phenyl siloxane) | 1.5330 |
| Poly(2-chloroethyl alpha-chloroacrylate) | 1.5330 |
| Poly(2-aminoethyl methacrylate) | 1.5370 |
| Poly(furfuryl metacrylate) | 1.5381 |
| Poly(butylmercaptyl methacrylate) | 1.5390 |
| Poly(1-phenyl-n-amyl methacrylate) | 1.5396 |
| Poly(N-methyl methacrylamide) | 1.5398 |
| Poly(cyclohexyl alpha-bromoacrylate) | 1.5420 |
| Poly(sec-butyl alpha-bromoacrylate) | 1.5420 |
| Poly(2-bromoethyl methacrylate) | 1.5426 |
| Poly(ethylmercaptyl methacrylate) | 1.5470 |
| Poly(N-allyl methacrylamide) | 1.5476 |
| Poly(1-phenylethyl methacrylate) | 1.5487 |
| Poly(2-vinyltetrahydrofuran) | 1.5500 |
| Poly(vinylfuran) | 1.5500 |
| Poly(methyl m-chlorophenylethyl siloxane) | 1.5500 |
| Poly(p-methoxybenzyl methacrylate) | 1.5520 |
| Poly(isopropyl methacrylate) | 1.5520 |
| Poly(p-isopropyl styrene) | 1.5540 |
| Poly(isoprene), chlorinated | 1.5540 |
| Poly(1-phenylallyl methacrylate) | 1.5573 |
| Poly(p-cyclohexylphenyl methacrylate) | 1.5575 |
| Poly(2-phenylethyl methacrylate) | 1.5592 |
| Poly(methyl m-chlorophenyl siloxane) | 1.5600 |
| Poly{1-(o-chlorophenyl)ethyl methacrylate)} | 1.5624 |
| Poly(1-phenylcyclohexyl methacrylate) | 1.5645 |
| Poly(methyl alpha-bromoacrylate) | 1.5672 |
| Poly(benzyl methacrylate) | 1.5680 |
| Poly{2-(phenylsulfonyl)ethyl methacrylate} | 1.5682 |
| Poly(m-cresyl methacrylate) | 1.5683 |
| Poly(o-methoxyphenol methacrylate) | 1.5705 |
| Poly(phenyl methacrylate) | 1.5706 |
| Poly(o-cresyl methacrylate) | 1.5707 |
| Poly(2,3-dibromopropyl methacrylate) | 1.5739 |
| Poly(1,2-diphenylethyl methacrylate) | 1.5816 |
| Poly(o-chlorobenzyl methacrylate) | 1.5823 |
| Poly(m-nitrobenzyl methacrylate) | 1.5845 |

-continued

| Polymer | Refractive Index |
|---|---|
| Bisphenol-A polycarbonate | 1.5860 |
| Poly(4-methoxy-2-methylstyrene) | 1.5868 |
| Poly(o-methyl styrene) | 1.5874 |
| Polystyrene | 1.5894 |
| Poly(o-methoxy styrene) | 1.5932 |
| Poly(diphenylmethyl methacrylate) | 1.5933 |
| Poly(p-bromophenyl methacrylate) | 1.5964 |
| Poly(N-benzyl methacrylamide) | 1.5965 |
| Poly(p-methoxy styrene) | 1.5967 |
| Poly(4-methoxystyrene) | 1.5967 |
| Poly{1,1-cyclopentane bis(4-phenyl)carbonate} | 1.5993 |
| Poly(vinylidene chloride) | 1.6000 |
| Poly(o-chlorodiphenyl methyl methacrylate) | 1.6040 |
| Poly{2,2-propane bis[4-(2,6-dichlorophenyl)]carbonate} | 1.6056 |
| Poly(pentachlorophenyl methacrylate) | 1.6080 |
| Poly(2-chlorostyrene) | 1.6098 |
| Poly(alpha-methylstyrene) | 1.6100 |
| Poly(phenyl alpha-bromoacrylate) | 1.6120 |
| Poly{2,2-propane bis[4-(2,6-dibromophenyl)cabonate]} | 1.6147 |
| Poly(2,6-dichlorostyrene) | 1.6248 |
| Poly(beta-naphthyl methacrylate) | 1.6298 |
| Poly(alpha-naphthyl carbinyl methacrylate) | 1.6300 |
| Poly(phenyl methyl silane) | 1.6300 |
| Poly(alpha-naphthyl methacrylate) | 1.6410 |
| Poly(p-phenylene ether-sulphone) | 1.6500 |
| Poly{diphenylmethane bis(4-phenyl)carbonate} | 1.6539 |
| Poly(vinyl phenyl sulfide) | 1.6568 |
| Poly(2-vinylnapthalene) | 1.6818 |
| Poly(N-vinyl carbazole) | 1.6830 |
| Naphthalene-formaldehyde rubber | 1.6960 |
| Phenol-formaldehyde resin | 1.7000 |

FIG. 1 illustrates, in section, a button, lens blank, or lens precursor (10) of the present invention. The shading 12 in FIG. 1 shows the gradient refractive index. In FIG. 1, the more darkly shaded area represents that part of the lens precursor having a higher refractive index. Thus, for example, lower refractive index zones or portions are shown at 14, while a higher refractive zone or portion is indicated at 16. The center of the lens blank or button is indicated at 18, while the gradient between the higher refractive index zone 16, and the lower refractive index zone or segment 14 is shown by bracket 20.

Figure 2:
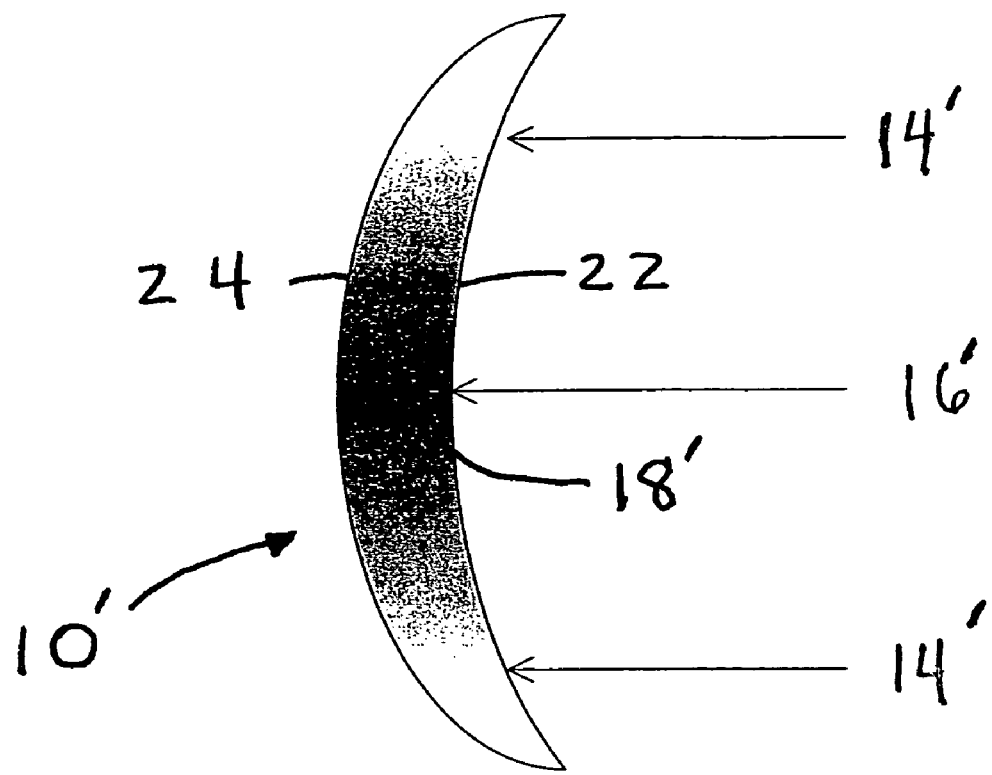
FIG. 2 illustrates a lens cut from an IRIG polymer button such as that shown in FIG. 1.

FIG. 2 shows schematically in section a lens 10', manufactured from the button or lens precursor shown in FIG. 1. Lower refractive index zones or regions 14' and a higher refractive index zone or region 16' also is shown. The line of focus or center of lens 10' is shown at 18'. The lens 10' of FIG. 2 would be manufactured from the lens precursor 10 of FIG. 1 in accordance with processes well-known to one skilled in the art. Lens 10' has, of course, anterior surface 24 and posterior surface 22. In accordance with well-known manufacturing principles of optics, the radius of curvature of anterior surface 24 and posterior surface 22, as well as the overall thickness of lens 10' is adjusted to determine lens focal length, power, and other optical parameters.

Figure 3:
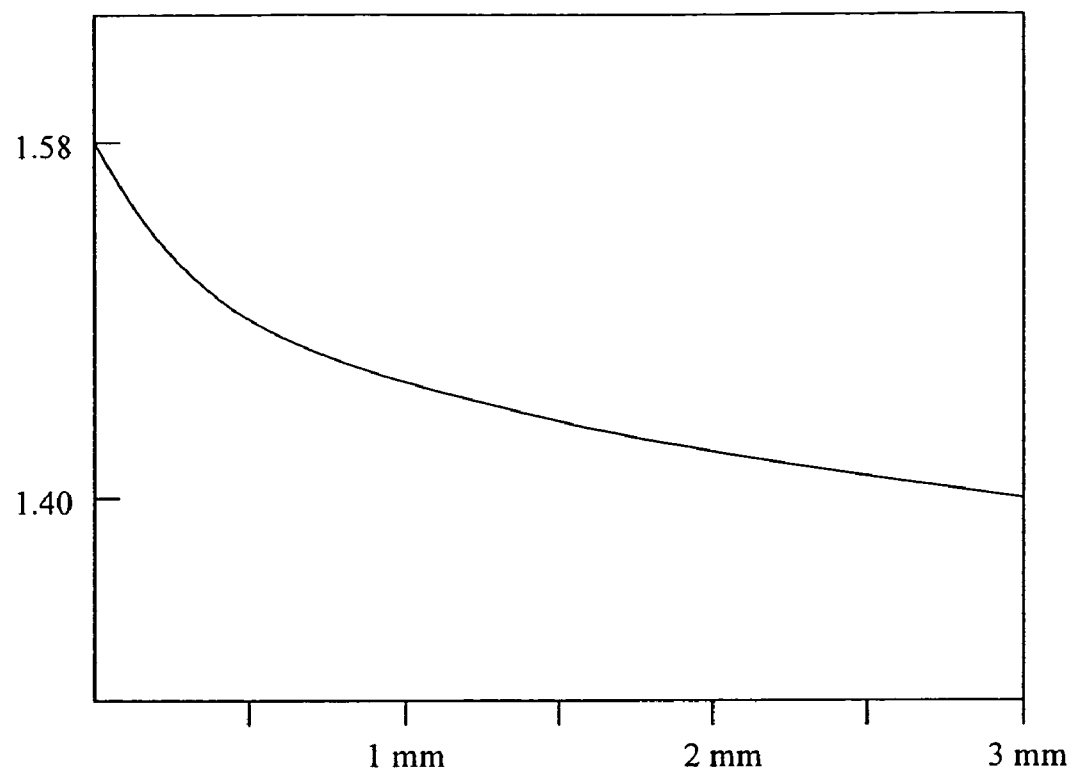
FIG. 3 shows refractive index of an IRIG polymer lens or ophthalmic device as a function of the distance from the center or line of focus of the device.

FIG. 3 shows the approximate refractive index profile of an IRIG polymer lens of the present invention as a function of distance from the center of the lens or line of focus of lens 10' in FIG. 2.

This invention will now be illustrated with reference to a number of examples. The examples are intended to be illustrative and not limiting. Thus, the attached claims should not be limited thereto.

TABLE 1

| Base Polymer Comp. | % Conc. | Second Polymer | RI | RI at center of lens | RI at 3.0 mm from center | RI at 5.0 mm from center |
|---|---|---|---|---|---|---|
| VC | 30 | 100% | 1.569 | 1.568 | 1.502 | 1.474 |
| LM | 37 | LM | | | | |
| HEMA | 30 | | | | | |
| EGDM | 2.92 | | | | | |
| DYA | 0.08 | | | | | |
| VC | 30 | 100% | 1.568 | 1.568 | 1.505 | 1.475 |
| LM | 37 | LM | | | | |
| HEA | 30 | | | | | |
| EGDM | 2.92 | | | | | |
| DYA | 0.08 | | | | | |
| VC | 30 | 100% | 1.563 | 1.554 | 1.498 | 1.469 |
| EHA | 37 | EA | | | | |
| HEMA | 30 | | | | | |
| EGDM | 2.95 | | | | | |
| DYM | 0.05 | | | | | |
| VC | 30 | 100% | 1.562 | 1.556 | 1.497 | 1.468 |
| EHA | 37 | EA | | | | |
| HEA | 30 | | | | | |
| EGDM | 2.95 | | | | | |
| DYM | 0.05 | | | | | |
| VN | 30 | 100% | 1.554 | 1.551 | 1.492 | 1.474 |
| EHA | 37 | EA | | | | |
| HEMA | 30 | | | | | |
| EGDM | 2.95 | | | | | |
| DYM | 0.05 | | | | | |
| VC | 29 | 100% | 1.551 | 1.550 | 1.482 | 1.474 |
| EHA | 37 | EA | | | | |
| HEA | 30 | | | | | |
| EGDM | 2.98 | | | | | |
| DOA | 0.02 | | | | | |
| VA | 1.0 | | | | | |
| Preferred Formulations | | | | | | |
| VC | 21.3 | 100% | 1.539 | 1.537 | 1.481 | 1.474 |
| HEA | 28.0 | LM | | | | |
| LM | 46.7 | | | | | |
| EGDM | 2.985 | | | | | |
| DOM | 0.015 | | | | | |
| VA | 0.7 | | | | | |
| MEB | 0.3 | | | | | |
| VC | 21.3 | 100% | 1.536 | 1.535 | 1.481 | 1.474 |
| HEA | 28.0 | LM | | | | |
| LM | 46.7 | | | | | |
| EGDM | 2.982 | | | | | |
| DOM | 0.018 | | | | | |
| VA | 0.7 | | | | | |
| MEB | 0.3 | | | | | |
| VC | 21.3 | 100% | 1.535 | 1.535 | 1.481 | 1.474 |
| HEA | 28.0 | LM | | | | |
| LM | 46.7 | | | | | |
| EGDM | 2.97 | | | | | |
| DOM | 0.03 | | | | | |
| VA | 0.7 | | | | | |
| MEB | 0.3 | | | | | |
| VC | 21.3 | 100% | 1.537 | 1.536 | 1.483 | 1.474 |
| HEA | 28.0 | LM | | | | |
| LM | 46.7 | | | | | |
| EGDM | 2.98 | | | | | |
| DOM | 0.02 | | | | | |
| VA | 0.7 | | | | | |
| MEB | 0.3 | | | | | |

VC: vinyl carbazole
VN: 2-vinyl naphthalene
EHA: 2-ethylhexylacrylate
LM: Lauryl methacrylate
HEMA; Hyroxyethylmethacrylate
HEA: Hydroxyethylacrylate
EA: Ethyl acrylate
EGDM: ethylene glycol dimethacrylate
VA: vinyl anthracene
MEB: 2-(2'-Methacryloxy-5'methylphenyl)benzotriazole
DYA: Disperse Yellow 7 Acrylate
DYM: Disperse Yellow 7 methacrylate
DOM: Disperse Orange 3 Methacrylamide General Preparation Steps for Polymers of Example 1-10

STEP 1: The comonomers listed above in Table 1 were mixed in a glass flask using a magnetic stir bar for at least 30 minutes followed by sonication for the times indicated, and then stirring again for another 30 minutes. The combination of sonication and hydrophilic/hydrophobic repulsion forces allows the formation of nanoclusters. The size of the nanoclusters is theoretically controlled by the amount of energy provided during these steps. We found that sonicating for about 30 minutes at a power setting of 100% on a Branson 5510 provides optically clear materials with adequate optical and physical properties. AIBN was added at a concentration of 0.2%. The comonomer mixture with was placed in a Teflon tubular mold. The mold was placed in water bath at 70° C. for 2 hours. A soft polymer rod measuring 6 mm in diameter and 6 inches in length was removed from the mold and cooled to room temperature.

STEP 2: The rod produced in step 1 was suspended e.g., by one end in the center of a cylindrical mold measuring 6 inches (15.24 mm) in length and 10 mm in diameter. A solution of the second lower RI, monomer containing 0.2% AIBN was poured around the 6 mm rod produced in step 1 and kept at 40° C. for 48 hours in an oven to allow for diffusion to occur. The mold is transferred to a water bath at 70° C. for 12 hours and then to an oven at 100° C. for 24 hours. A final polymer rod measuring 6 inches (15.24 mm) in length and 10 mm in diameter and having a IRIG was produced. The polymer rod was machined into 17 mm×2 mm disks and IOLs were cut from the samples. The IOLS produced by this method are foldable and have good optical properties.

The refractive index was measured using a CLR 12-70 refractometer from Index Instrument. To asses the diffusion progression, RI was measured at three distances from the center of the IOL: 0 mm (center of the lens), 3.0 mm, and at 5.0 mm.

The results show that the RI decreases radially from the centre to the periphery of the lens in a manner similar to that of a young human lens. The fickian nature of diffusion of the lower refractive index monomer into the higher refractive index base material creates an IRIG.

It goes without saying that while the present invention has been described with reference to a lower RI monomer permeating or diffusing into a higher RI base material or base polymer, the reverse also is contemplated. In that variation a higher RI monomer would be diffused into a lower RI base material in accordance with the steps of the method of this invention.

Multifocal/Accommodating IOLs Made from IRIG Polymer

Current multifocal IOLs offer acceptable near and far vision but suffer from the following problems:
1. Poor intermediate vision
2. Loss of light hitting the retina
3. Visual artifacts such as halos, light scattering, and glare
4. No accommodation These shortcomings are mainly caused by the limited number of refractive zones created on the surface of the lens. In contrast with the natural lens where refraction and accommodation is mainly afforded by a RI gradient throughout the bulk of the lens. The purpose of this invention is to create an IOL that simulates the gradient RI present in a young natural crystalline lens.

IRIG Multifocal/Accommodating IOL Preparation

IOLs with a 6 mm diameter were cut from IRIG polymer rods prepared by the method described above. The refractive index at a distance r from the center of the lens may be evaluated by the following formula:

$$n(r)=n_0(r)[-\tan h(gr)sech(gr)]$$

Where g is a gradient constant and $n_0$ is the refractive index at the center of the lens.

Unlike "layered" GRI materials, the refractive index at any distance from the center follows a continuous progression evidenced by the integral function.

The lens power may be calculated from the index of refraction using the formula:

$$P=-(t/r)\times(dn/dr)$$

Where t is the thickness of the lens and r is the radial distance.

For example, a lens with a central power $P_0$ and a transition zone between $r_1$ and $r_2$ will have the following power function:

$$P(r) = \begin{cases} P_0 & \text{if } r \leq r_1 \\ P_0(r_2-r)/(r_2-r_1) & \text{if } r_1 < r \leq r_2 \\ 0 & \text{if } r > r_2 \end{cases}$$

What is claimed is:

1. A method for making an infinite refractive index gradient (IRIG) ophthalmic device having an edge and a center and a refractive index which decreases or increases infinitesimally forming a continuum of refractive index values from ophthalmic device edge to center, the method comprising the steps of:
   providing an at least partially polymerized polymer rod having a first refractive index, the rod being formable into an ophthalmic device;
   suspending the rod in an ophthalmic device monomer having a second refractive index when polymerized, the monomer permeating into the rod from the exterior to the interior to provide a gradient;
   reacting the monomer with the polymer of the rod to create a rod-like structure with an infinite refractive index gradient; and
   forming the rod-like structure into an IRIG ophthalmic device.

2. An infinite refractive index intraocular lens (IOL), the IOL having a refractive index decreasing from the center of the lens to its edge wherein the IOL is obtained by the method of claim 1.

3. An infinite refractive index IOL, the IOL having a refractive index increasing form the center of the lens to its edge wherein the IOL is obtained by the method of claim 1.

* * * * *